United States Patent [19]

Weissman

[11] Patent Number: 5,066,230

[45] Date of Patent: Nov. 19, 1991

[54] DENTAL PRODUCT COMBINING A REAMER TOOL AND ANCHOR POST

[76] Inventor: Bernard Weissman, 225 East 48th St., New York, N.Y. 10017

[21] Appl. No.: 273,299

[22] Filed: Nov. 18, 1988

Related U.S. Application Data

[63] Continuation-in-part of Ser. No. 172,483, Mar. 24, 1988, Pat. No. 4,990,088.

[51] Int. Cl.⁵ .............................. A61C 3/02; A61C 5/04
[52] U.S. Cl. .................................. 433/165; 433/221; 433/225; 433/102
[58] Field of Search ............... 433/224, 220, 221, 165, 433/102, 225

[56] References Cited

U.S. PATENT DOCUMENTS

| Re. 29,817 | 10/1978 | Lieb et al. | 433/221 |
|---|---|---|---|
| 3,524,255 | 8/1970 | Kurer | 433/221 |
| 3,894,339 | 7/1975 | Manzi | 433/166 |
| 3,919,774 | 11/1975 | Fishman | 433/224 |
| 4,205,444 | 6/1980 | Weissman | 433/165 |
| 4,219,620 | 8/1980 | Carse | 433/225 |
| 4,255,145 | 3/1981 | Weissman | 433/165 |
| 4,270,903 | 6/1981 | Nash | 433/165 |
| 4,334,865 | 6/1982 | Borle | 433/221 |
| 4,365,958 | 12/1982 | Vlock | 433/225 |
| 4,408,990 | 10/1983 | Misch | 433/224 |
| 4,449,937 | 5/1984 | Weissman | 433/225 |
| 4,515,565 | 5/1985 | Winter-Moore et al. | 433/221 |
| 4,728,292 | 3/1988 | Lustig et al. | 433/225 |

FOREIGN PATENT DOCUMENTS

2812175  9/1979  Fed. Rep. of Germany ...... 433/221

Primary Examiner—Robert P. Swiatek
Assistant Examiner—Nicholas D. Lucchesi
Attorney, Agent, or Firm—Barry G. Magidoff; Paul J. Sutton; Anthony Amaral

[57] ABSTRACT

There is provided a combination dental tool for forming a bore in a tooth stub and which can then be used for the anchoring of a dental prosthesis to the stub. The combination tool is formed having a first cutting end portion and an opposite, and second, holder end portion, to be held by a dental handpiece. The holder portion is formed adjacent a crown anchor portion and the holder portion can be removed after the bore is formed. Preferably, the crown anchor portion is formed of a softer material which can be readily formed to the desired shape for the prosthesis. The cutting portion preferably has alternating sections of larger and smaller diameter and has laterally facing cutting surfaces to form undercut portions along the bore to aid in firmer seating of the anchor post.

12 Claims, 5 Drawing Sheets

DENTAL PRODUCT COMBINING A REAMER TOOL AND ANCHOR POST

This is a continuation-in-part of application Ser. No. 172,483, filed Mar. 24, 1988, now U.S. Pat. No. 4,990,088.

BACKGROUND OF THE INVENTION

The present invention relates to a combination product which combines the utility of a tool and a prosthesis support post for use in dentistry, and more particularly to a product which first can be used as a dental tool which provides for the drilling of a bore hole and for the forming of lateral undercuts along the interior longitudinal surface of the bore hole into a tooth canal, and which can be rotated by a dental handpiece associated with a dental drill, and at least a portion thereof can then be maintained within its own drill-hole as an anchor, or support, post for a dental prosthesis.

It is well known in the dental field to provide a drill tool bit for forming a bore hole through the root canal of a tooth. It is also common to grind away the upper surface of the tooth, using a dental grinding tool to provide space for a dental prosthesis to be anchored to the tooth via an anchor post extending into and cemented within the bored out root canal. Such dental anchors are generally cemented into the bore hole and in some cases the anchors are provided with undulating lateral surfaces to further assist in securing the anchor to the cement. It has been found, however, that the security of the dental prosthesis may be compromised by a failure of the cement holding the anchor in the bore, as well as by the difficulty of seating the prosthesis around a projecting portion of the anchor and onto the top of the tooth. Further problems can be created by the use of an improperly matched anchor post for the reamer diameter, especially where a passive anchor post is desirable.

SUMMARY OF THE INVENTION

Accordingly, it is an object of the present invention to provide a dental tool which combines the effectiveness of a bore drill, or reamer, and an undercutting routing tool, and can act as the prosthesis anchor post, to provide improved accuracy of fit and for the security of the cemented anchor within the tooth. It is a further object of the present invention to optimally provide on the tool a counterboring portion to enlarge the outer end of the bore. It is a further object of the present invention to provide all of these effects by a single tool, which can then be reformed into the anchor post, thus permitting not only efficiency in the number of tools required, but also simplifying the problem of maintaining the accuracy of fit and the integrity of, and desired mutual relationships between, the bore hole and the cemented anchor post in the bore hole.

These and other objects are achieved in accordance with the present invention wherein the combination dental device includes a first holder end portion designed to be receivable in a dental tool holder, such that the dental tool holder can rotate the dental tool; a second drilling, or reaming, end portion tapering longitudinally endwardly to a minimum effective diameter at the second end and providing an axially facing cutting surface for forming a bore of sufficient diameter in a tooth of a patient, upon rotation of the tool, to receive an anchor post; a drill shank portion extending from the drilling end portion towards the holder portion and preferably including at least two alternating longitudinally extending shank sections, the first drill shank section having laterally facing cutting surfaces and a relatively larger effective diameter, and the second drill shank section having a smaller effective diameter and a non-cutting surface such that the application of laterally directed force to the tool while the tool is being rotated within the bore of the tooth provides for the routing out of notches, or undercut surfaces, along the interior of the bore in the direction of the laterally directed force. The drilling end of this tool is intended to include means for forming a hole by drilling, as well as reaming means to enlarge the tooth root canal.

There is further preferably provided, at a portion intermediate the drill shank portion and the first holder end, a divergent counterbore drilling section capable of forming an enlarged bore diameter at the outer end of a bore hole in a tooth, and a planar grinding surface.

The first holder end portion of the tool is designed to be removably secured to a conventional dental handpiece so as to be rotatably driven from the handpiece. The tool is to be secured into the handpiece such that it will maintain its position upon the application of longitudinal force exerted toward the second drilling end of the tool and upon the exertion of lateral force while the tool is being rotated as described in the above-identified copending application.

Immediately adjacent to the maximum diameter end of the counterbore, and extending towards the holder end, is a prosthesis core support portion which preferably has a maximum diameter at least about equal to the maximum effective diameter of the counterbore.

In one embodiment, where the prosthesis core support portion diameter is not significantly larger than the maximum effective diameter of the counterbore, a prosthesis core can be built up around the core support portion, which may have to be shortened by removing the holder end, if necessary. In another embodiment, the maximum core support diameter is significantly larger than the counterbore and an e.g., all metal core unitary with the anchor post can be prepared by working and shaping the core support portion by known means. In this latter situation, the axially facing surface of the core support portion is a planar grinding surface for cutting down and levelling the tooth surface and surrounding the counterbore to support the prosthesis.

The core anchor section preferably tapers inwardly towards the holder end and can be rippled, or scored, to present undercuts to improve adhesion of the core anchor section to composite or cement material forming a core for the immediate support of a crown, or prosthesis, above the tooth stub. If the core anchor section has a diameter sufficient to form a unitary core, the undercuts are to be added after the section has been cut and shaped to accept the crown prosthesis.

After the bore hole is reamed, and routed out to form the undercuts, the reamer is replaced into its self-drilled hole, and cemented into place as an anchor post. The holder end extends above the bore, and serves as a useful handle for manipulating the anchor post until the post is cemented in place.

Any pre-formed undercuts in the core anchor section are to be limited in depth so as not to reduce the structural strength of the reamer such that it would not be able to withstand the stress of boring. After the drilling end is cemented into the bore hole, the portion protruding above the bore hole can be trimmed and cut to the desired size using a conventional edge grinder disk, for example, and undercuts can be added.

The combination dental tool and post of the present invention is to be used with a conventional dental tool handpiece as providing support and driving power for the device. The size and shape of the holder end is thus necessarily limited by the requirements of conventional handpieces.

As used in the process of this invention, the drill point, or reamer, is placed at the exposed root canal opening of a tooth. The tooth has been reduced to approximately the desired height above the gum line by removing broken or decayed dental material. The combined tool post is held by a conventional dental handpiece and the power applied to rotate the tool at low speeds in a conventional manner, pressing downwardly against the tooth to bore out a hole of the desired depth. This procedure is especially useful for preparing a tooth for the placing of a crown on an anterior mandibular or maxillary tooth.

It is well known in the dental field to select a drill, or reamer, of a proper length and diameter to obtain the desired size bore hole. For the present invention, however, the length of the drill shank is preferably carefully calibrated with the desired depth of the bore, as the drill shank is preferably inserted substantially completely into the bore hole, such that the counterbore portion of the tool forms a funnel-shaped enlargement of the entrance to the bore hole, by reaming out a counterbore, and the planar grinding surface, if present, can grind to a level plane the surface of the tooth. In addition, the core post shank should extend above the top surface of the tooth to form the central support for the prosthesis core. The enlarged counterbore is preferably provided at the zone of greatest stress, at the interface of the ground down tooth and the crown.

After a hole is bored out to the desired depth, using the preferred tool of the present invention, the tool is withdrawn a short distance above the bottomed out position, and lateral pressure exerted by the tool on the sides of the bore, preferably alternately and only in the facial and lingual directions. In this manner, the enlarged first shank sections rout out laterally undercut notches at the spaced positions of such first sections along the bore, in the preferred lingual and facial directions. It is noted that the tool preferably does not widen the cross-section around the entire circumference of the inner bore in the tooth, but only elongates those portions contacted by the cutting surfaces of the first sections of the drill shank portion in the direction in which lateral pressure is exerted.

The combination tool/post is withdrawn from the bore hole and disconnected from the handpiece. The drill shank is then inserted back into the bore, leaving the core post shank extending beyond the tooth. Cement is packed into the bore hole with the post in the conventional manner, but surrounding the anchor post, and extending into the bore hole undercuts, securing the post in the bore hole; the holder end portion is then usually cut off from the anchored post at the desired length. The core anchor section, if large enough, can be shaped and cut to the proper size to serve as a unitary core for a crown. The security of the cemented seal is improved by the interaction between the routed out undercuts in the bore and the varying diameter along the drill shank.

Further details of the present invention are shown in the accompanying drawings, by way of example and not by way of exclusion. Many portions of the invention or the context therefor are shown in schematic representation, where greater detail is unnecessary, as it will be apparent or well-known to those skilled in the art. Referring to the accompanying drawings.

Figure 1:
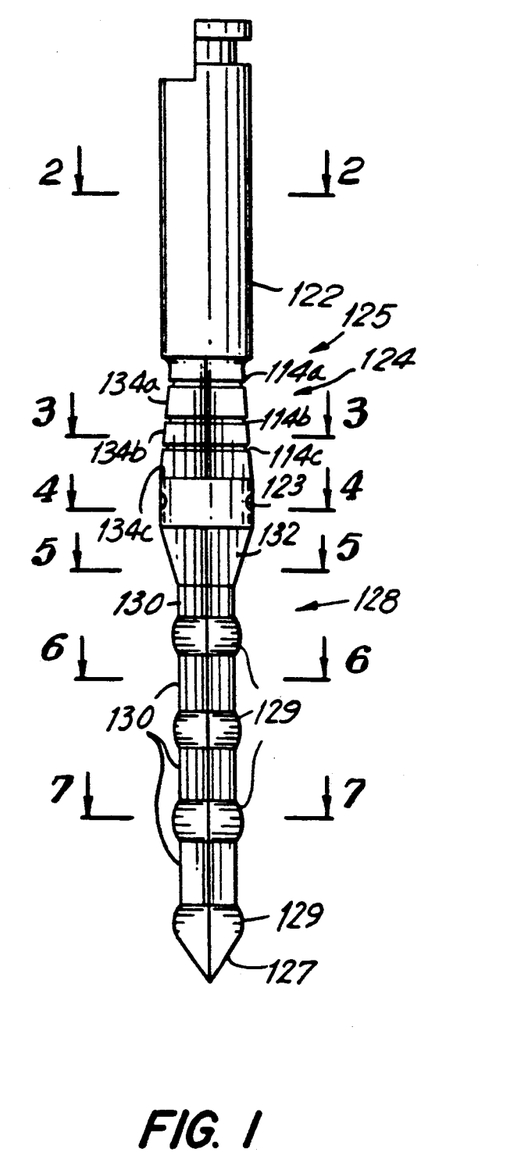
FIG. 1 is a side elevation view of one embodiment of the present invention.
Figure 2:
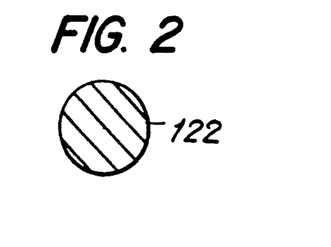
FIG. 2 is a cross-section view along line A—A of FIG. 1.
Figure 3:
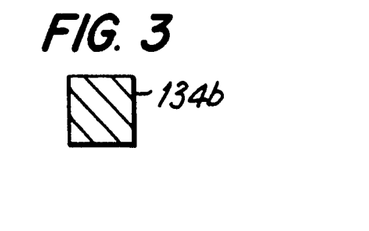
FIG. 3 is a cross-section along line B—B of FIG. 1.
Figure 4:
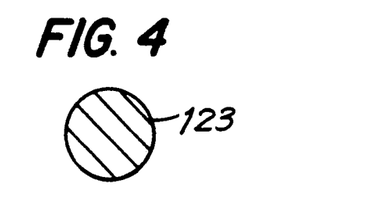
FIG. 4 is a cross-sectional view of the embodiment of FIG. 1 taken along lines C—C.
Figure 5:
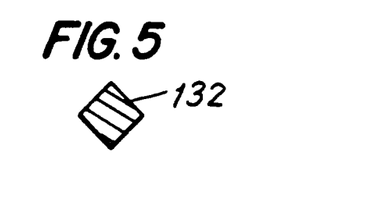
FIG. 5 is a cross-sectional view of the embodiment of FIG. 4 taken along lines D—D.

Referring to the drawings, a combination reamer tool and post, indicated by the numeral 125 is shown having a reaming, or drilling, first pointed end 127, a drill shank portion, indicated by the numeral 128, comprising a plurality of cutting and routing sections 129, separated by a plurality of relatively smaller diameter shank stop sections 130. Located immediately adjacent the innermost stop section 130 is the divergent counterbore section 132. Immediately adjacent the maximum diameter of the counterbore section 132, and extending axially towards the holder end 122 is a cylindrical core post shank section 123, and immediately adjacent thereto, and tapering inwardly towards the holder portion 122, is the rippled or undercut core anchor section, generally indicated by the numeral 124. A holder end portion 122 extends outwardly from the core anchor post section 124.

The outer section of the holder end portion 122 is of conventional design suitable for being secured to conventional dental handpieces, and can be adapted for whichever dental handpiece is to be used.

The cross-sections of the cutting portions 132, 129, 127 are preferably substantially square. The cross-section of the core post shank 123 is round as can be the cross-sections of the smaller diameter intermediate shank stop sections 130; these latter sections are herein shown as square in the drawings.

Figure 6:
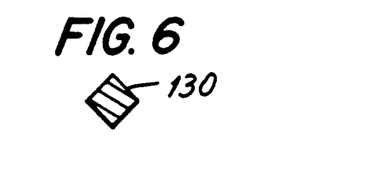
FIG. 6 is a cross-sectional view of the embodiment of FIG. 4 taken along lines E—E.
Figure 7:
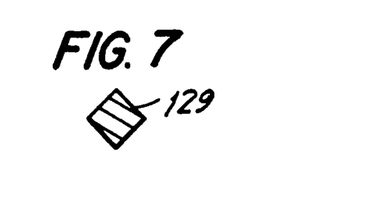
FIG. 7 is a cross-sectional view of the embodiment of FIG. 4 taken along lines F—F.

The cutting portions of the tool 128 of FIG. 1, include the lower drilling end 127, the counterbore portion 132, and the larger routing shank sections 129. The smaller diameter shank stop sections 130 do not include a lateral cutting surface, such as are present on the routing shank sections 129. The various cutting surfaces and the drilling point end 127 can be coated with a hard, fine granular substance, such as diamond dust. The cross-sectional views of FIGS. 6 and 7 show that both the routing sections 129 and the intermediate, smaller diameter shank stop sections 130, are substantially square in cross-section.

Both of the embodiments depicted in the drawings are provided with laterally cutting routing sections 129, having an outer surface forming a substantially continuous curve in an axial direction, between two smaller diameter intermediate stop sections 130. The curved cutting surfaces of the routing sections 129 can be also optionally coated with hard, fine granular material, such as diamond dust, if desired.

The combination tool and post 125 can alternatively be formed having cross-sections of various other regular polygons, as desired, the apices of the polygons in the routing sections 129, drill point 127, and counterbore 132, providing the cutting edges. Included within the scope of such polygonal cross-sections are shapes having at least one curved side, such as so-called half-round or quarter-round shapes. Preferably, the polygons have no more than six sides. When the term "diameter" is used for such polygonal cross-sections, it refers to the "effective diameter", i.e., the diameter of a bore hole cut by such sections rotating about a single axis.

The core post shank 123 is substantially circular in cross-section, being substantially cylindrical in overall shape. The core anchor section 124 is substantially a truncated pyramid in overall shape, having substantially square cross-sections, with the apices rotated about 45° relative to the apices of the drill shank section 128. The undercut portions 114, have a substantially reduced diameter, providing for more secure adhesion to the core composite cement.

If desired, the combination device of the present invention can be fabricated with marked segments, or score lines, indicating units of length. For example, the segments on the anchor core section, or the individual drill routing sections, can be formed to a specific length, e.g., 1 mm. This permits readily cutting or grinding the drill or reamer to the desired length by merely counting segments.

The initial reaming out of the tooth root canal is carried out not only by the end drilling portion 127 but by the leading routing ring section 129.

Figure 8:
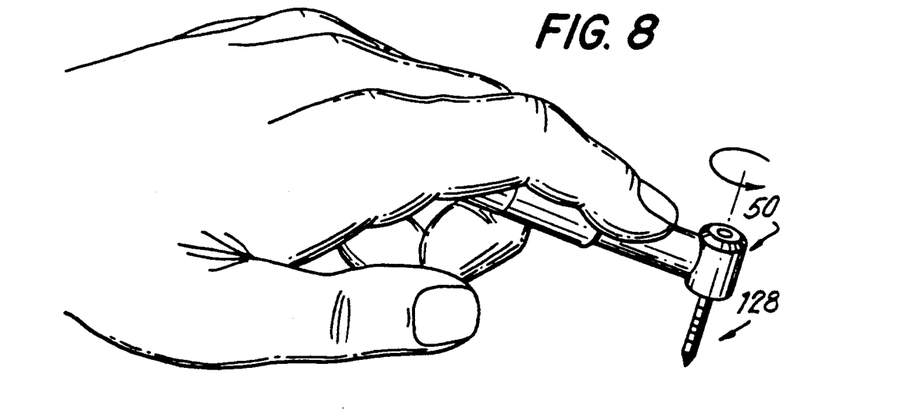
FIG. 8 is a perspective view showing a tool of the present invention being held while rotating.
Figure 9:
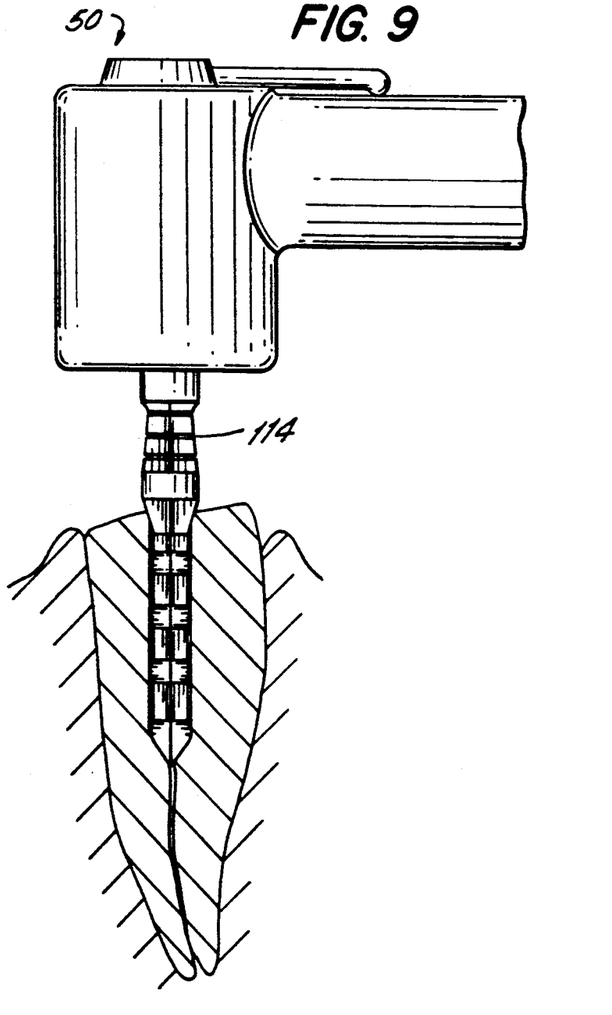
FIG. 9 is a cross-section elevation view showing a tool of the present invention almost fully deployed within the bore of the tooth stub.

Referring to FIG. 8, and to FIG. 9, wherein the combination tool of the present invention is located within a bored hole, the tool 125, is operatively supported and held by a conventional handpiece, generally indicated by the numeral 50. The handpiece is of a conventional type, which can provide support and carry the driving power to the tool 125 to cause it to rotate. The handpiece 50 can securely hold and mechanically drive the tool 125, while being subjected to longitudinal forces exerted axially into the tooth, during a reaming out operation, or while being subjected to force applied laterally, and against the lateral interior surfaces of the bore, during a routing operation. Such hand pieces are well-known, and can, e.g., be air- or motor-driven, or directly gear driven, by straight or right angle dental rotary devices.

Figures 14, 15:
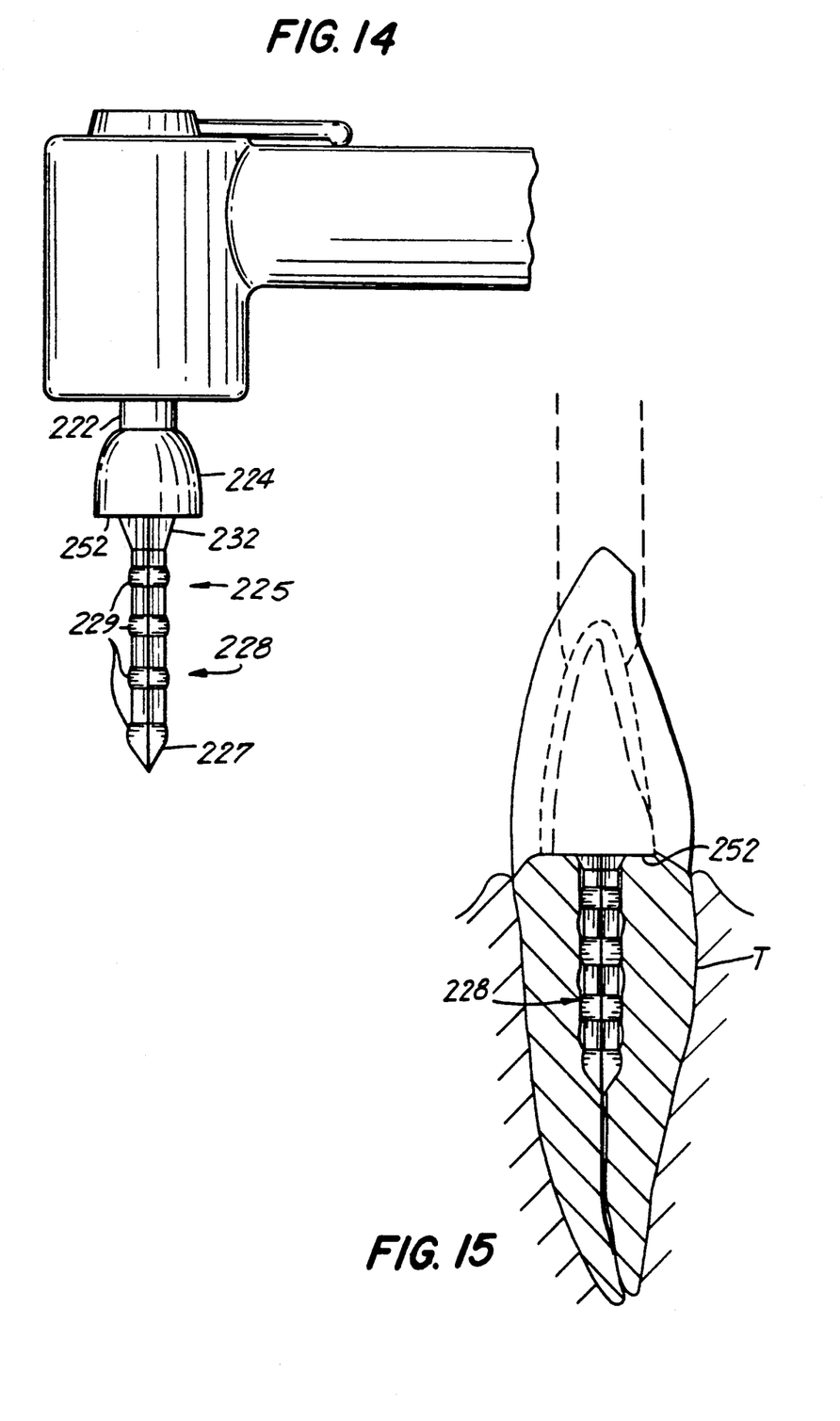
FIG. 14 is a side elevation view of another embodiment of the tool of the present invention in a handpiece.
FIG. 15 is an elevation cross-section view showing a unitary crown core, or supporting foundation, formed from the embodiment of FIG. 14, in a tooth.

Referring to FIG. 14, a combination tool is shown, generally indicated by the numeral 225, wherein the anchor core section 224 is substantially larger than that of the counterbore 232. A planar grinding surface 252 is formed defining the edge of anchor core 224 and extending annularly about the counterbore maximum diameter. The drill shank 228 is substantially similar to that of the first embodiment of FIG. 1, and all of the cutting surfaces 227, 229, 232 and the grinding surface 252 can be formed of similar hard materials and coated with the hard granular material, such as diamond dust.

Figure 10:
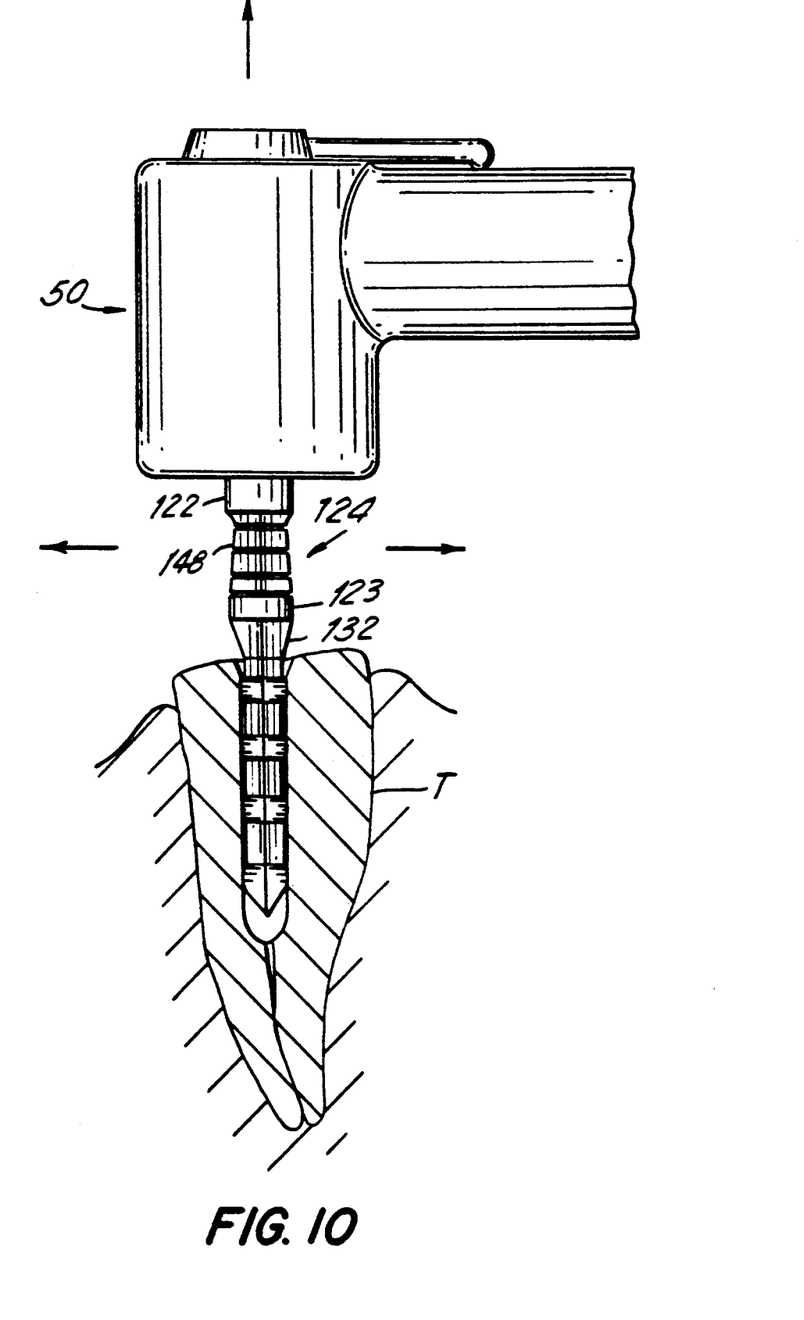
FIG. 10 is a side elevation view, in partial cross-section, of a tool of the present invention held by a conventional dental handpiece in the first stage of the routing procedure of the present invention.

In carrying out the procedure in accordance with the present invention, after the bore is fully formed in the tooth, as shown by FIG. 9, including an enlarged counterbore at the top surface of the tooth, the tool 128 is lifted above its bottommost position, as shown in FIG. 10, such that the counterbore 13 is above the top surface of the tooth. Lateral pressure is exerted from the handpiece 50 through the tool 125 and against the inside of the tooth bore, while the tool 125 is continuously rotated at the desired speed. Such pressure is preferably exerted successively in the lingual and facial directions, such that the grinding rings 129 are forced against the sides of the bore, routing out undercut surfaces, or notches, along the surface of the bore in those directions. The pressure is exerted first in one of the preferred directions and then in the other of the lingual and facial directions.

The router portions 129 are preferably approximately 25% larger in diameter than the second, lesser diameter stop sections 130, such that upon fully routing out the undercut notches, the notches have a major elliptical diameter approximately 50% greater than the original bore hole diameter. The maximum diameter of the counterbore 132 is preferably at least 50% larger than that of the router sections 129, and the diameter of the planar grinding surface 252 is at least about 50% larger again.

Figure 11:
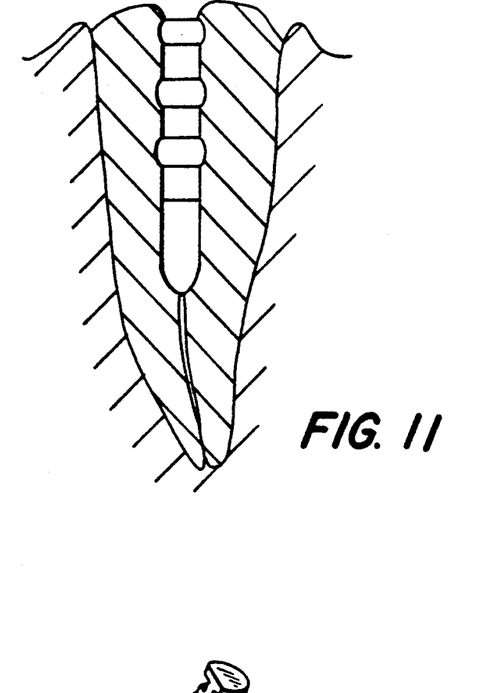
FIG. 11 is an elevation cross-section view of the dental tool of the present invention withdrawn from a fully reamed and routed bore of a tooth (shown in cross-section) in accordance with the present invention.
Figure 12:
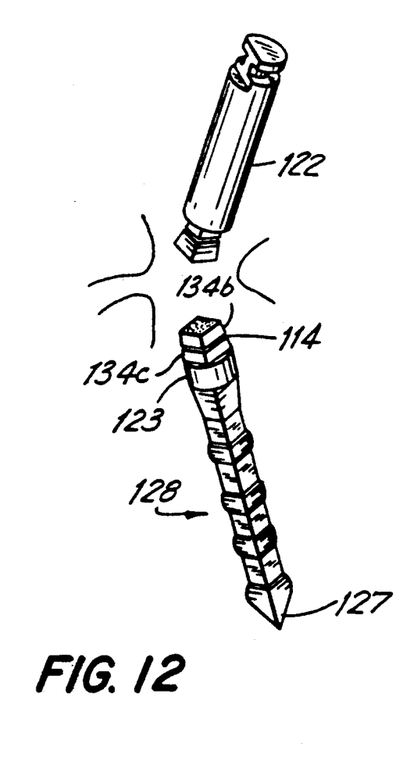
FIG. 12 is a perspective view of a dental anchor post being formed from the reamer-router tool in accordance with the present invention.
Figure 13:
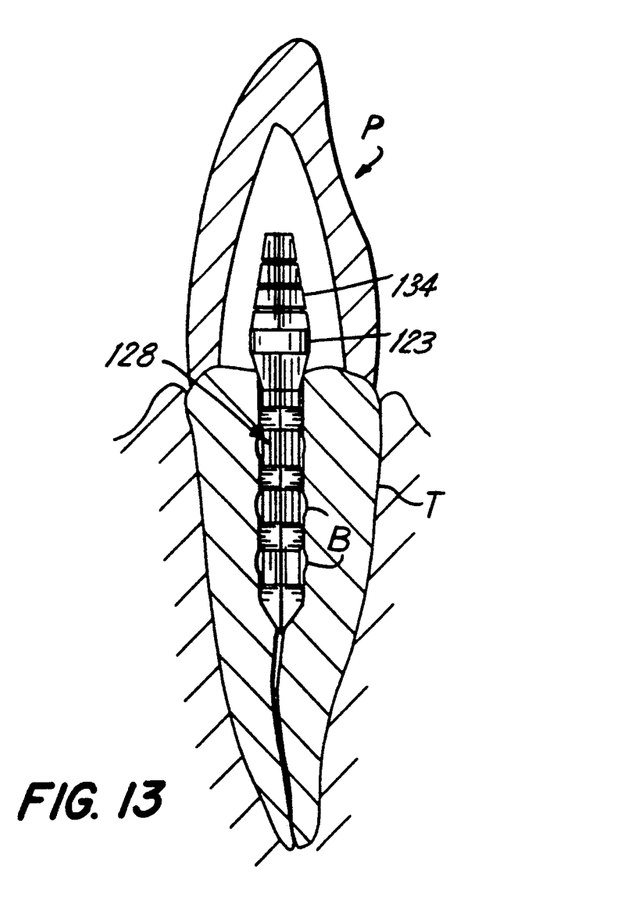
FIG. 13 is an elevation cross-section view of a completed tooth prosthesis, including the anchor post formed according to the present invention.

A fully reamed and routed out reduced tooth T, from which the reamer has been withdrawn, is shown in FIG. 11. The reamer 125 is removed from the handpiece 50, and the portion comprising the counterbore 132, the drill shank 128 and drill tip 127 is reinserted into the reamed and routed out tooth bore, as the anchor post base, as shown in FIG. 13, and cemented in place.

The anchor post base 128 is inserted into the prepared bore hole, with cement to secure the anchor in place. The inherently accurate size relationship between the bore hole and the anchor post diameters, permits this anchor post 128 to be readily used as a so-called "passive" anchor, where the post need not be screwed in place into the bore hole. The post 128 merely drops passively, or is gently pushed, into the bore. As shown in FIGS. 13 and 15, the larger diameter router sections 129, 229 are not juxtaposed with the routed out, undercut tooth bore sections (B). In this manner, the cement has been found to more securely hold the anchor post in place.

Extending outwardly from the tooth bore is the core anchor post, which comprises the cylindrical core post shank 123 and the convergent anchor 127 section 124, and the holder end 122, which anchors a tooth prosthesis, P. If necessary, the protruding holder end 122 is cut down to the desired length beyond the surface of the bore hole, and to the desired shape, and then cemented integrally with a core to support the desired crown prosthesis.

In FIG. 15 there is depicted a crowned tooth prepared with a unitary anchor post and crown core 228, 224, made of an integral piece of material; the anchor core section 224 is shaped and sized (from its original shape shown in dashed lines) to the core size shown in the drawing, by well known dental fabricating means. This unitary core can directly retain and secure that crown prosthesis by being cemented to the crown directly.

The present invention not only reduces the number of individual items the dentist must keep in stock and sterilize for use, but also avoids the problem of a misfit between the anchor post base and the bore hole.

Although the particular shape of the core anchor post 121 shown, is not a necessary feature of this invention, the combination of the cylindrical core post shank 123 and the undercut tapered pyramidal core anchor section 124, provides an especially secure, core anchor post beneath a composite core.

The particular shape of the drill cutting segments 132, 128, 127 of this combination dental product is also not critical to the invention. For example, any of the drill shank embodiments described in the above-identified co-pending application can be used with this invention, and can be used as the anchor post base. A straight, constant diameter, drill shank can be provided, if desired.

It is understood that the core anchor section 124 and the core post shank 117, or the unitary core 224, need not be made of the same material as the rest of the combination product, i.e., the holder end 122 and drill shank 128 (which is inserted into the tooth bore). For example, titanium alloy, or other hard and tough material, such as stainless steel, is the material of choice for the drill shank 128, i.e., that portion of a prosthesis anchor to be inserted into the tooth bore. The core anchor portions 117, 124, or unitary core 224, however, can be formed of the same metal or of a softer, more easily shaped material, such as a ceramic dental material, a polymer composite, or a ceramic/metal or polymer/metal laminate, or another metal, for example. The undercut core anchor section 124, or the unitary core section 224, should, however, have sufficient torsional strength to withstand the stress of rotary drilling. All of these anchor post materials, as well as other materials well-known to the art, can be formed as a unit with the drill shank and counterbore portion by well-known means, such as welding, soldering, or casting or molding together.

The patentable embodiments of the invention which are claimed are as follows:

1. A combination cutting tool and anchor device for attachment to a tooth, or the like, comprising:
    a first holder end portion designed to be receivable in a dental tool holder such that the dental holder can rotate the cutting tool; a second drilling end portion having a proximal end and a distal tip end relative to the holder end portion, the drilling end tapering longitudinally endwardly from a maximum diameter at the proximal end to a minimum effective diameter at the distal tip end, the drilling end portion having a polygonal cross-section which provides axially facing cutting edges for drilling a bore into a tooth of a patient upon rotation of the tool; a shank portion extending intermediate the two end portions and including a first and a second axially successive, longitudinally extending shank sections; the first such shank section having laterally facing cutting surfaces and a relatively larger effective diameter, the laterally facing cutting surfaces of the first shank section being defined by a substantially continuous curve, extending axially from the intersection with the second shank section; and the second shank section having a relatively smaller diameter relative to the first shank section and to the maximum diameter of the drilling end portion, such that upon the application of a laterally directed force while rotating the tool within a previously drilled bore, undercut portions are routed out from the interior surface of the bore, and
    a crown anchoring means portion located intermediate said holder end portion and the shank portion, for anchoring a dental prosthesis with respect to a tooth; the combination device being formed as a integral, rigid unit, but the crown anchoring means being formed of a softer, more easily shaped material than the shank.

2. A combination dental tool product providing for drilling and grinding and for final anchoring of a dental prosthesis to a tooth stub, the combination tool product comprising a first holder end portion designed to be receivable in a dental tool holder such that the dental tool holder can rotate the dental tool; a second drilling end portion having a proximal end and a distal tip end relative to the holder end portion, the drilling end tapering longitudinally from a maximum effective diameter at the proximal end to a minimum effective diameter at the distal tip end, the drilling end portion having a polygonal cross-section, which provides axially facing cutting edges for drilling a bore into a tooth of a patient upon rotation of the tool; a drill shank portion extending intermediate the two end portions and including a first and a second intersecting, longitudinally extending, axially successive shank sections, the first such shank section having laterally facing cutting edges, a relatively larger effective diameter, and a polygonal cross-section; and the second such shank section having a relatively smaller diameter relative to the first shank section and to the maximum diameter of the drilling end portion; the intersection of the first and second shank sections of the tool being at an angle not less than a right angle; such that upon the application of a laterally directed force while rotating the tool within a previously drilled bore, undercut portions are routed out from the interior surface of the bore by the first shank section; and a core anchor post portion intermediate the drill shank portion and the holder end portion; the core anchor post comprising a core anchor section, the core anchor section having a plurality of undercut circumferential zones axially arrayed, the combination dental tool product being an integral unit.

3. The combination dental tool in accordance with claim 2, further comprising a divergent counterbore cutting portion having cutting surfaces of continuously increasing diameter, and extending from adjacent the drill shank portion towards the core anchor section, the counterbore cutting surfaces effective diameter increasing to a maximum towards the core anchor section.

4. The combination dental tool of claim 3, wherein the core anchor post portion further comprises a substantially constant diameter core post shank extending longitudinally between the core anchor post portion and the maximum diameter end of the counterbore cutting portion.

5. The combination dental tool of claim 4, wherein the shape of the lateral cross-section of the core post shank is substantially circular and the diameter of the core post shank is at least equal to that of the maximum counterbore cutting portion diameter.

6. The combination dental tool of claim 5, wherein the shape of the lateral cross-section of the first shank section is an equilateral polygon.

7. The combination dental tool of claim 5, wherein the shape of the lateral cross-section of the core anchor section is an equilateral polygon.

8. The combination dental tool of claim 7, wherein the shape of each of the lateral cross-sections of the counterbore, drill shank and core anchor portions is a square.

9. A combination dental tool product providing for drilling and grinding and for final anchoring of a dental prosthesis to a tooth stub, the combination tool product comprising a first holder end portion designed to be receivable in a dental tool holder such that the dental tool holder can rotate the dental tool; a second drilling end portion tapering longitudinally endwardly to a minimum effective diameter at the tip and providing an axially facing cutting surface designed to bore out the root canal of the tooth; a drill shank portion extending from adjacent the drilling end portion towards the holder end portion and including at least a first and a second successive longitudinally extending shank sections, the first such shank section having laterally facing cutting surfaces and a relatively larger effective diameter, and the second such shank section having a relatively smaller diameter; a core anchor post portion having a core anchor section adjacent the holder end portion and extending towards the drill shank portion; and a divergent counterbore cutting portion having cutting surfaces of continuously increasing diameter, and extending from adjacent the drill shank portion towards the core anchor section, the counterbore cutting surfaces effective diameter increasing to a maximum towards the core anchor section; the core anchor post portion further comprising a substantially constant diameter core post shank extending longitudinally between the core anchor section and the maximum diameter end of the counterbore cutting portion; and wherein the shape of the lateral cross-section of the post shank is substantially circular and has a diameter at least equal to that of the maximum counterbore diameter; wherein the shape of the lateral cross-section of the core anchor section is an equilateral polygon and wherein the apices of such polygon are circumferentially offset from the apices of the other polygon cross-section portions of the tool product.

10. The combination dental tool of claim 9, wherein the cross-section of the core anchor section converges towards the holder end portion.

11. A method of securing a dental prosthesis integral with a tooth, comprising the steps of;
    operably securing to a dental handpiece a combination device, the combination device comprising a shank formed with a cutting end portion an opposite end holder portion capable of being received within and held by a dental handpiece for rotating said combination device, and an intermediate crown anchoring means portion formed of a softer more easily shaped material;
    causing said device to rotate while in contact with a tooth surface, thereby causing said cutting portion to form a bore within said tooth,
    releasing said combination device from said handpiece, removing the end holder portion,
    applying first cement means to the cutting end portion and securing said cutting end portion and cement means within the bore;
    shaping the crown anchoring means portion to form a shaped crown anchoring means; and
    applying second cement means to said shaped crown anchoring means and securing a dental prosthesis to the crown anchoring means so that the prosthesis appears to be integral with said tooth.

12. A method of building a superstructure onto a excavated surface of a healthy reduced tooth, the method comprising boring out the tooth root canal to form a bore hole utilizing a mechanically driven rotating reaming tool, the tool comprising a first holder end portion designed to be receivable in a powered dental tool holder such that the dental tool holder can rotate the reaming tool; a second drilling end portion tapering longitudinally endwardly to a minimum effective diameter at the tip and providing an axially facing cutting surface for drilling a bore into a tooth of a patient upon rotation of the tool, and a drilling shank portion extending from the second end portion towards the first end portion; and a core anchor portion intermediate the first end portion and the drilling shank portion; the hole being bored by driving the reaming tool in a rotary manner to reach the full depth of the desired bore hole; disconnecting the tool from its powered holder and passively placing the drilling portion wholly within the bore hole and cementing the tool in place; removing portions of at least the holder end of the tool to properly size the core anchor portion of the tool extending beyond the bore hole, and securing a crown, or dental prosthesis, to the core anchor portion.

* * * * *